Figure 1:
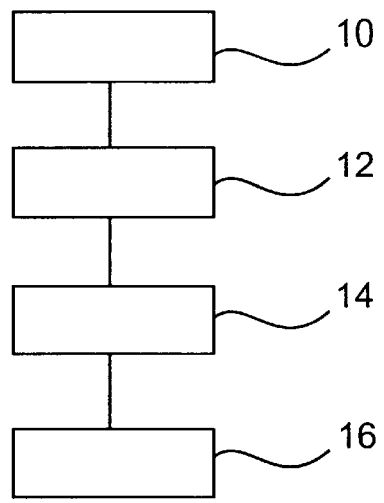

United States Patent
Berger

Patent Number: 5,989,477
Date of Patent: Nov. 23, 1999

[54] PROCESS FOR THE CHEMICAL MODIFICATION OF SOLIDS CONTAINING ALKYL GROUPS

[75] Inventor: Steffen Berger, Düsseldorf, Germany

[73] Assignee: Arplas Gesellschaft Für Plasmatechnologie mbH, Weissandt-Gölzau, Germany

[21] Appl. No.: 08/836,916

[22] PCT Filed: Nov. 23, 1995

[86] PCT No.: PCT/EP95/04621

§ 371 Date: May 23, 1997

§ 102(e) Date: May 23, 1997

[87] PCT Pub. No.: WO96/15853

PCT Pub. Date: May 30, 1996

[30] Foreign Application Priority Data

Nov. 24, 1994 [DE] Germany ............... 44 43 240

[51] Int. Cl.⁶ .................................. B01J 19/12
[52] U.S. Cl. .................. 264/446; 264/483; 264/489; 427/573; 204/157.15; 204/165
[58] Field of Search .................... 264/446, 483, 264/489; 427/573; 204/157.6, 157.15, 157.87, 157.88, 157.89, 157.9, 164, 165

[56] References Cited

U.S. PATENT DOCUMENTS

2,167,718  8/1939  Harris, Jr. et al. .

FOREIGN PATENT DOCUMENTS

| 0 122 289 | 10/1984 | European Pat. Off. . |
| 0 593 988 A1 | 4/1994 | European Pat. Off. . |
| 41 41 805 A1 | 6/1993 | Germany . |
| 61-069804 | 4/1986 | Japan . |
| 1 326 197 | 8/1973 | United Kingdom . |
| WO 94/03263 | 2/1994 | WIPO . |
| WO 95/03344 | 2/1995 | WIPO . |

OTHER PUBLICATIONS

Noller, Chemistry of Organic Compounds, p. 205, 1965.
Chemical Abstracts, 26473d., vol. 81, No. 6, Aug. 12, 1974.

*Primary Examiner*—Jan H. Silbaugh
*Assistant Examiner*—Kenneth M. Jones
*Attorney, Agent, or Firm*—Finnegan, Henderson, Farabow, Garrett & Dunner, L.L.P.

[57] ABSTRACT

The invention relates to a process for the chemical modification of solids containing alkyl groups. It is provided that the solids containing alkyl groups are heated to temperatures above their melting point and subjected to a plasma treatment in a frequency range from 10 kHz to 10 GHz.

13 Claims, 1 Drawing Sheet

PROCESS FOR THE CHEMICAL MODIFICATION OF SOLIDS CONTAINING ALKYL GROUPS

The invention relates to a process for the chemical modification of solids containing alkyl groups, and to chemically modified solids containing alkyl groups.

It is known that solids containing alkyl groups, for example polyolefins and waxes, can be used in many fields. Use, for example, as coating materials, hot-melt adhesives etc., is possible. For the processability of the solids containing alkyl groups in the most varied fields of use, these solids must be mixed with certain additives which are latched to the particular field of use. Because of the multiplicity of possible fields of application, a comprehensive uniform use of the solids containing alkyl groups is thus impossible.

Kunststoff-Taschenbuch, 25th edition, pages 248 to 259, discloses a process for the aftertreatment of solids containing alkyl groups. In this process, the surface of the solid containing alkyl groups, for example a PE surface, is treated with a high-voltage plasma, in order to achieve a local chemical modification. Owing to this local surface treatment, for example in the case of moldings, an improvement in the coatability or printability is achieved. However, it is a disadvantage in this case that an additional aftertreatment must be performed, the application of which is possible only to a restricted extent owing to the provision of a high-voltage plasma unit for the finished product.

The object therefore underlying the invention is to create a process of the generic type by which a chemical modification of solids containing alkyl groups is possible in a simple and inexpensive manner.

According to the invention, this object is achieved by heating the solids containing alkyl groups to temperatures above their melting point and subjecting them to a plasma treatment in a frequency range from 10 kHz to 10 GHz. Surprisingly, it was found that owing to the conversion of the solids containing alkyl groups into a melt and their plasma treatment, a modification of material properties can be specifically induced within the solids containing alkyl groups. Owing to the conversion into a melt, a qualitatively and quantitatively higher grade chemical modification may be achieved. In particular, by means of the plasma treatment of the melt of the solids containing alkyl groups, special chemical products can be achieved which can be used in a versatile manner without requiring a further complex aftertreatment. A degree of the chemical modification of the solids containing alkyl groups may preferably be achieved in a simple manner by adjusting a viscosity of the melt and/or parameters of the plasma treatment.

In an advantageous development of the invention it is provided that the plasma treatment is carried out with alternating frequencies, preferably with combinations of different alternating frequencies. Thus, the plasma treatment can be carried out highly advantageously with successively selectable frequencies, with alternately selectable different frequencies, with at least two simultaneously selectable different frequencies, and combinations of frequency selections resulting therefrom. By this means, the chemical modification can highly advantageously be matched to the different chemical structure of the solids containing alkyl groups used and to their application by the chemical modification.

In a further advantageous development of the invention, it is provided that the plasma treatment is carried out with supply of at least one inert gas, for example helium and/or argon, and/or with supply of at least one reaction gas, for example oxygen and/or nitrogen. It is further preferred if the plasma treatment is carried out in succession with an inert gas plasma and at least one reaction gas plasma and/or a reaction gas plasma mixture or with supply of a mixture of at least one inert gas and one reaction gas. By choosing a composition of the process gas during the plasma treatment (inert gas, reaction gas, reaction gas mixture) which is matched to the solids which contain the alkyl groups and are to be modified, it is possible to incorporate, to a sufficient extent, the reactive groups necessary for the chemical modification, for example hydroxyl groups, carboxyl groups, primary and secondary amino groups, into the melt of the solids containing alkyl groups. These incorporated groups are able to react with the solids containing alkyl groups and to enter into chemical bonds and/or to adhere physically. Further polar, but unreactive groups which can be incorporated, for example carbonyl groups, tertiary amino groups, can likewise effect a modification in properties of the solids containing alkyl groups. By converting the solids containing alkyl groups into the melt, a relatively homogeneous modification of the solids containing alkyl groups is possible by means of the reactive or unreactive groups incorporated during the plasma treatment.

The melt solidified after the plasma treatment thus has a relatively homogeneous distribution of reactive or unreactive groups introduced over the entire spatial extent of the solid containing alkyl groups. Any type of solids containing alkyl groups can thus be achieved which are suitable, after the plasma treatment, for specific applications, a further subsequent treatment no longer being necessary. The adjustment of the solids containing alkyl groups to their special application can be performed in a simple manner by the plasma treatment according to the invention of a melt of the solids containing alkyl groups.

In a further advantageous development of the invention, it is provided that the solids containing alkyl groups are admixed prior to the plasma treatment with solid and/or liquid reactants, auxiliaries and additives. The solid and/or liquid reactants, auxiliaries and additives can preferably also be admixed to the melt of the solids containing alkyl groups. By means of this optional addition of said reactants or substances, the chemical modification of the solids containing alkyl groups can be matched precisely to a specific application.

It is further advantageous if the solids containing alkyl groups are converted into the melt prior to the plasma treatment. As a result, the melt can be generated separately, if appropriate admixed with the reactants or auxiliaries and additives and then subjected to the plasma treatment. By this means, the process steps of generating the melt of the solids containing alkyl groups and the plasma treatment can be carried out separately, that is successively, with each of the two process steps being able to be optimized separately, that is can be matched to the specific solid containing alkyl groups. This substantially avoids interactions between the two process steps. This is advantageous, in particular, if the solids containing alkyl groups have different melting points or if a variable melt viscosity is to be set. Furthermore, the unit for carrying out the plasma treatment can be kept free from the apparatus for generating the melt, so that the unit can be used in a varied manner.

However, it is also within the context of the invention that the melt of the solids containing alkyl groups is produced during the plasma treatment, that is, therefore, simultaneously. This enables the plasma treatment, that is the chemical modification of the solids containing alkyl groups, to be begun before they have been fully heated above their melting temperature. By this means it becomes advantageously possible to stop the process step of conversion of the solids containing alkyl groups into their melt at a point in time at which not all of the solids containing alkyl groups have yet been liquified. By this means, the reactive or unreactive groups can be incorporated by means of the plasma treatment into the solids containing alkyl groups at differing intensities in different spatial areas of the solid containing alkyl groups. Thus, after solidification of the melt, solids containing alkyl groups may be achieved which have undergone different chemical modification in different areas.

Further advantageous developments result from the remaining features mentioned in the subclaims.

Figure 2:
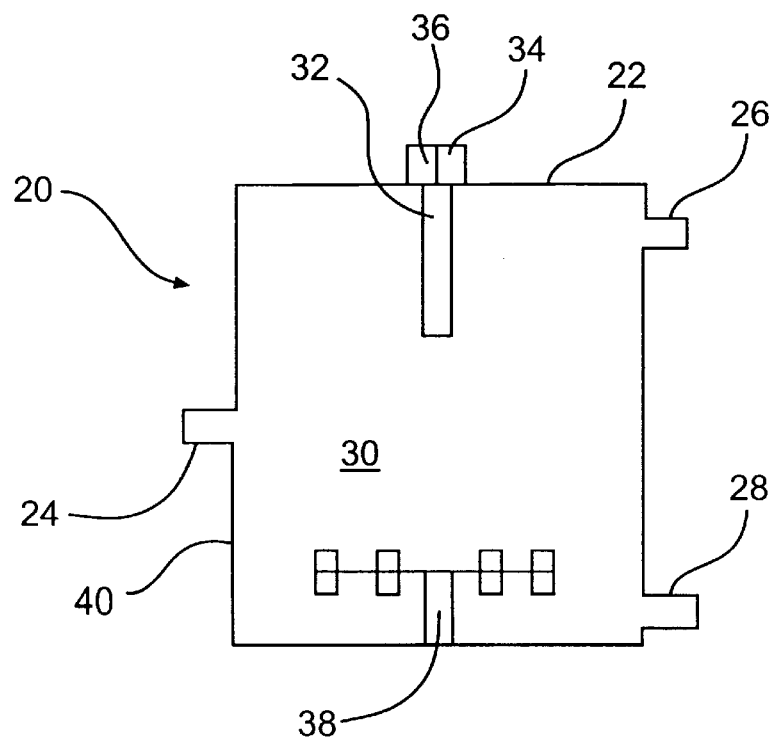

The invention is described below in more detail in illustrative examples with reference to the associated drawings. In the drawings:

FIG. 1 shows a process sequence of the chemical modification of a solid containing alkyl groups and FIG. 2 shows a diagrammatic representation of an arrangement for carrying out the process.

FIG. 1 is intended to clarify the process according to the invention using a diagram. In a first step, solids containing alkyl groups available as starting materials are prepared. The solids containing alkyl groups can be present either in powder or granule form or as shaped articles. In the process step 10, the solids containing alkyl groups are heated above their melting point by exposure to a heat source, so that these are converted into a melt. During the process step 10, the solids containing alkyl groups can be admixed with reactants, auxiliaries and/or additives. This admixture can be performed either prior to the melting, during the melting or after the melting.

In a next step 12, the process gasses and process parameters desired for the plasma treatment of the melt are set. In this case, in particular the specific combinations of the process gasses are established, that is a first treatment with an inert gas plasma, preferably with helium and/or argon, and the subsequent treatment with a reaction gas plasma, preferably with oxygen and/or nitrogen, or else the treatment with a plasma which is generated from a mixture of the abovementioned gasses. In addition, the high frequencies necessary for the plasma generation in vacuo and their time course are set. Variants are thus conceivable in which a plasma treatment is carried out initially at a lower frequency, for example 13.56 MHz, and then at a higher frequency, for example 2.4 Ghz [sic]. Furthermore, alternating addition of the process gasses is possible, that is the inert gas, the reaction gas and/or a mixture of a reaction gas and an inert gas. In addition, an alternating, if appropriate alternatively simultaneous selection, of different frequencies can be preset. Furthermore, the desired process pressure, which is, for example, in the range between 0.1 mbar and 2 mbar, is set. During the plasma treatment, the process pressure can be subject to process-specific fluctuations. Furthermore, the duration of treatment for which the plasma treatment of the melt takes place is established. This is, for example, between 5 seconds and 15,000 seconds. Said process parameters and process gasses can be varied in any combination among one another and are matched, in particular, to the composition of the respective solid containing alkyl groups which is actually present.

In a subsequent process step 14, the plasma treatment of the melt of the solids containing alkyl groups is performed using the process parameters or process conditions set in the process step 12. It is conceivable in this case that, during the plasma treatment, the process parameters can be modified and/or adapted, for example by a controller. Furthermore, during the process step 14, the melt can be mixed or stirred. By this means, a more homogeneous mixing of the melt with the reactive or unreactive groups incorporated by the plasma treatment is possible. Furthermore, the melt can be subjected to controlled heating during the plasma treatment, so that solidification or change in the melt viscosity during the plasma treatment is avoided. However, by means of targeted controlled heating of the melt, it is also possible to change the viscosity during the plasma treatment, for example to increase or to decrease the viscosity, in order to influence in this manner the incorporation via the plasma treatment of the reactive or unreactive groups.

In a subsequent process step 16, the melt is further processed. This further processing can comprise, for example, solidification of the melt. The chemically modified solids containing alkyl groups then present can, for example, be granulated, compressed to form defined shaped articles or processed in other ways. Furthermore it is conceivable that the chemically modified melt is further processed prior to the solidification. This can be performed, for example, by means of an extruder, an injection molding machine, a shock cooler, a mixing unit for producing solutions, dispersions, emulsions, compounds and/or blends, an impregnating device, a spraying or injection device and/or a device for producing composites. The direct further processing of the chemically modified melt avoids the need for otherwise necessary intermediate steps, for example the solidification and remelting necessary prior to further processing. However, in the context of the present description, details of a further processing of the modified melt are not to be considered more closely.

FIG. 2 shows diagrammatically a unit for the chemical modification of solids containing alkyl groups. The unit is designated generally by 20 and is shown in a greatly simplified manner. The unit 20 comprises a reactor 22 which has at least one inlet port 24 for the solids containing alkyl groups to be modified. The inlet port 24 can also be used for the addition of the reactants, auxiliaries and/or additives. In addition, the reactor 22 has an inlet port 26 for process gasses or plasmas. The inlet port 26 can have a plurality of part-inlets, which are not shown here, via which either an inert gas, a reaction gas and/or a mixture of an inert gas and a reaction gas or corresponding plasmas can be passed into the reactor 22. In addition, the reactor 22 has an outlet 28 for the treated solids containing alkyl groups. The reactor 22 can be sealed hermetically, so that a vacuum can be generated in an interior 30 of the reactor 22, with details here not being further considered. An electrode 32 projects into the interior 30, which electrode is coupled to a generator 34 for the microwave plasma excitation and to a high frequency feed 36. The electrode 32 can consist of a plurality of part-electrodes, with one being able to be designed for the microwave plasma excitation and one for the high frequency feed. The shape of the electrode 32 can be, for example, rod-shaped, spherical, half-shell-shaped etc. In addition, an agitator 38 is arranged in the interior 30. The agitator 38 is only present optionally, so that its presence is not necessary for the chemical modification according to the invention. Furthermore, the reactor 22 can be heatable, either via its outer shell 40 or via the agitator 38 which can have the corresponding heating elements.

The arrangement 20 shown here is only exemplary and can be replaced by any other suitable arrangement by means of which the process according to the invention can be carried out.

The unit 20 shown in FIG. 2 performs the following function:

Via the inlet port 24, the reactor 22 is charged with the solids containing alkyl groups. According to a first process variant, the solids containing alkyl groups are still in their solid state, so that these are, for example, tipped into the reactor 22. The solids containing alkyl groups can in this case be present, for example, as granules, powder or else as relatively large shaped articles. The interior 30 of the reactor 22 is then exposed to thermal energy, for example by means of a heating of the outer shell 40. By means of this heating, the solids containing alkyl groups charged into the interior 30 are heated above their melting point, so that a melt results in the interior 30. This melt can be stirred by means of the agitator 38.

According to a further process variant, the agitator 38 is dispensed with, so that the melt settles on the bottom of the reactor 22 within the interior 30.

After the solids containing alkyl groups have been converted into their melt, a plasma treatment of the melt is carried out by means of the electrode 32 with simultaneous feed of a process gas via the inlet port 26. The electrode 32 can in this case be alternately excited with different frequencies. For this purpose, this electrode is alternately coupled to the generator 34 or to the high frequency feed 36. If appropriate, two electrodes 32 are present, one of the respective electrodes being coupled to the generator 34 and the other to the high frequency feed 32. These can then be selected alternately. The process gas fed via the inlet port 26 leads, in a known manner, to the formation of a plasma within the interior 30 of the reactor 22. A variable plasma depending on the composition of the process gas is generated. In this case, either an inert gas, a reaction gas or mixture of an inert gas and a reaction gas or corresponding plasmas can be fed to the reactor 22 via the inlet port 26. The inlet port 26 is designed in such a way that the feed of the inert gas and/or of the reaction gas and/or of the mixture of the inert gas and the reaction gas or of the corresponding plasmas can be varied during the plasma treatment via control elements which are not to be considered here in more detail. That is, for time periods of different length, different amounts of each process gas required or of the corresponding plasmas can be fed to the reactor 22.

After the plasma treatment of the melt has been completed, this melt is removed from the reactor 22 via the outlet port 28. In order that the melt does not solidify during the plasma treatment and during the discharge, the supply of heat can be continued during the plasma treatment. The melt exiting from the outlet port 28 can then be fed to further processing or treatment. However, in the context of the present description, this possibility is not to be considered further.

According to a second process variant, the melt of the solids containing alkyl groups is generated outside the reactor 22. The melt is therefore generated externally in a suitable device and charged in this state into the interior 30 of the reactor 22. The reactor 22 merely requires for this purpose a heat source which is suitable for being able to expose the melt during treatment to heat energy sufficient so that it maintains a temperature above its melting point.

According to a third process variant, the melt of the solids containing alkyl groups can be generated separately in a vessel which is then introduced into the reactor 22 through a suitable inlet port. After plasma treatment of the melt has been carried out, this vessel can again be removed from the reactor 22, so that the inlet port 24 and the outlet port 28 can be omitted. By means of this variant, the structure of the reactor 22 can be optimized exclusively to the generation of the plasma.

According to a further mode of operation, it is conceivable to operate the reactor 22 in the continuous-flow principle. That is, solids containing alkyl groups are continuously fed via the inlet port 24, which solids, depending on the outfitting of the reactor 22, are already present as melt or are converted into a melt within the reactor 22. The melt then present is then subjected to the plasma treatment within a section of the reactor 22 designed for the plasma treatment and then removed via the outlet port 28.

The various process variants for plasma treatment of a melt described here are merely exemplary. It must be made clear, that the actual structure of a unit 20 for carrying out the process according to the invention can be highly variable. The critical factor is that the solids containing alkyl groups are converted into a melt prior to the plasma treatment. The unit 20 merely needs to be designed for feeding the solids containing alkyl groups, either as solid or as melt, and removing the treated melt.

In a specific example, a known PE wax 720 (HOECHST) is introduced as powder into a mold. The height of the powder layer within the mold is approximately 3–4 mm. The mold is then introduced into a heating apparatus, for example a furnace, and heated there to temperatures of approximately 160° C. By this means, the PE wax is heated above its melting point. The mold remains in the furnace until the PE wax is completely molten. The mold containing the PE wax present in a melt is then introduced into the reactor 22, this reactor having neither the inlet port 24, the outlet port 28 nor the agitator 38.

Within the reactor 22, the melt of the PE wax is subjected to a plasma treatment having the following process parameters:

A process pressure of 0.7 mbar is set. The power of the high frequency feed 36 is 600 W, and the power of the generator 34 for the microwave excitation is 1,200 W. The generator 34 generates a frequency of 2.45 GHz and the high frequency feed 36 generates a frequency of 13.56 MHz. Argon is fed as inert gas into the interior 30, a high-frequency excitation being performed for a time period of 30 seconds and a microwave excitation being performed for 30 seconds. Oxygen is then fed as reaction gas and a plasma treatment is carried out for 60 seconds with a high-frequency excitation and for 60 seconds with a microwave excitation. Nitrogen is then fed as a further reaction gas and, likewise, a high-frequency excitation is carried out for 60 seconds and a microwave excitation is carried out for 60 seconds. The entire plasma treatment of the melt of the PE wax thus lasts 300 seconds.

After completion of the plasma treatment, the melt is removed from the reactor 22 and cooled, so that a wax plate is formed. This wax plate has a chemical modification with respect to the original PE wax, which was effected by a structural change during the plasma treatment. By means of the treatment with the process gas plasmas (inert gas plasma, reaction gas plasma) oxygen- and nitrogen-containing polar groups were incorporated into the melt. Owing to the incorporation of the polar groups in the wax melt, the PE wax after solidification exhibits a structural change.

This structural change is manifested, for example, by a change in the surface tension values of the resulting wax plate. By applying test inks, it was demonstrated that surface tension values between approximately 28 mN/m and approximately 41 mN/m were present on the top of the plate, whereas surface tension values between approximately 32 mN/m and approximately 41 mN/m were present on the bottom of the plate. The local difference in surface tension values between the top and bottom of the treated wax plate results from defective mixing of the melt during the plasma treatment. The resulting local differences can be minimized—as mentioned—by mixing the melt during the plasma treatment.

I claim:

1. A process for the chemical modification of a solid containing alkyl groups, which process comprises the steps of:

(a) providing a starting material comprising a solid containing alkyl groups;

(b) heating the starting material to a temperature greater than the melting point of the solid to form a melt;

(c) subjecting the melt to a plasma treatment carried out at alternately applied different frequencies in the range of from 10 kHz to 10 GHz, the plasma treatment being carried out in a reaction zone under treating conditions effective to incorporate into the melt reactive groups or unreactive groups; and (d) solidifying the plasma-treated melt to obtain a product containing a chemically modified solid containing alkyl groups.

2. A process for the chemical modification of a solid containing alkyl groups, which process comprises the steps of:

(a) providing a starting material comprising a solid containing alkyl groups;

(b) heating the starting material to a temperature greater than the melting point of the solid to form a melt;

(c) subjecting the melt to a plasma treatment carried out with combinations of different frequencies alternately applied in the range of from 10 kHz to 10 GHz, the plasma treatment being carried out in a reaction zone under treating conditions effective to incorporate into the melt reactive groups or unreactive groups; and (d) solidifying the plasma-treated melt to obtain a product containing a chemically modified solid containing alkyl groups.

3. The process according to claim 1 or claim 2, wherein at least one inert gas is supplied to the reaction zone.

4. The process according to claim 1 or claim 2, wherein at least one reaction gas is supplied to the reaction zone.

5. The process according to claim 1 or claim 2, wherein the plasma treatment is fed successively with at least one inert gas plasma, followed by at least one reaction gas plasma or a reaction gas mixture plasma or with a mixture of at least one inert gas and at least one reaction gas.

6. The process according to claim 1 or claim 2, wherein there is employed an alternating plasma treatment with at least one inert gas plasma, at least one reaction gas plasma and at least one mixture of an inert gas/reaction gas plasma.

7. The process according to claim 1 or claim 2, wherein at least one of the solid containing alkyl groups and the melt is admixed with one or more reactants, auxiliaries or additives prior to the solidification step.

8. The process according to claim 7, wherein the admixing is performed at one or more of the times prior to, during, and after the plasma treatment.

9. The process according to claim 1 or claim 2, wherein the plasma treatment is carried out at a process pressure of from 0.1 mbar to 2 mbar.

10. The process according to claim 1 or claim 2, wherein the duration of the plasma treatment is between 5 seconds and 15,000 seconds.

11. The process according to claim 1 or claim 2, wherein the solids containing alkyl groups are converted into a melt of variable viscosity.

12. The process according to claim 1 or claim 2, wherein the solids containing alkyl groups which have been converted into the melt are mixed or stirred during the plasma treatment.

13. The process according to claim 1 or claim 2, wherein the solids containing alkyl groups is selected from the group consisting of polyolefins and waxes.

* * * * *